United States Patent

Bashir-Hashemi

[11] Patent Number: 5,998,661
[45] Date of Patent: Dec. 7, 1999

[54] PREPARATIONS OF ORGANIC NITRO COMPOUNDS THROUGH MIXED OXIDIZING AGENTS

[75] Inventor: Abdollah Bashir-Hashemi, Bridgewater, N.J.

[73] Assignee: The United States of America as represented by the Secretary of the Army, Washington, D.C.

[21] Appl. No.: 09/100,782

[22] Filed: Jun. 15, 1998

[51] Int. Cl.⁶ .......................... C07C 205/00; C07C 61/08
[52] U.S. Cl. ..................... 562/434; 568/924; 568/927; 568/939; 568/941; 562/507; 562/553
[58] Field of Search ...................... 568/924, 939, 568/941, 927; 562/434, 507, 553

[56] References Cited

U.S. PATENT DOCUMENTS

| | | | |
|---|---|---|---|
| 5,214,221 | 5/1993 | Bashir-Hashemi | 568/944 |
| 5,214,222 | 5/1993 | Bashir-Hashemi | 568/945 |
| 5,241,116 | 8/1993 | Bashir-Hashemi | 562/867 |
| 5,378,333 | 1/1995 | Bashir-Hashemi | 204/157.65 |

FOREIGN PATENT DOCUMENTS 1199351  2/1969  United Kingdom .

*Primary Examiner*—Paul J. Killos
*Assistant Examiner*—J. Parsa
*Attorney, Agent, or Firm*—John Moran; John Callaghan

[57] ABSTRACT

A process for selective, direct oxidation of amine or amine hydrochloride compounds is described. It uses mixed oxidizing agents of monopersulfate and ozone.

8 Claims, No Drawings

5,998,661

PREPARATIONS OF ORGANIC NITRO COMPOUNDS THROUGH MIXED OXIDIZING AGENTS

SUMMARY OF THE INVENTION

The direct oxidation of primary amines to the corresponding nitro derivatives is very useful because it provides for preparation of nitro organic compounds that are otherwise difficult to synthesize by direct nitration methods. The invention is an improved method for the preparation of organic nitro compounds by oxidation of the corresponding amine or amine hydrochloride groups that are subtituents on the organic substrate. The oxidation process of this invention is selective and is able to oxidize amine groups that otherwise resist reaction.

DESCRIPTION OF THE INVENTION

The method comprises conducting the oxidation of the organic amine or amine hydrochloride with a combination of ozone and monopersulfate compounds as the oxidizing agents. This selectively forms the corresponding nitro compounds. The organic amine or amine hydrochloride salt will be dissolved in a solvent system such as water-acetonitrile or water or water-acetone. The reaction media will be at a pH of about 6–7. The reaction temperature will be from about 0 to about room temperature. The substrate of the organic compound may be polycyclic such as bicyclic or tetracyclic. It may be aromatic. The substrate may have different functional groups besides the target amine groups. The other functional groups can, for example, be carboxylic groups, nitro groups or other oxygen containing groups. An advantage of the invention is that it selectively oxidizes the amino group to the nitro group while leaving the remainder of the compound intact.

The practice of the invention is illustrated by the following examples.

EXAMPLE 1

Preparation of Nitro Adamantane 1-aminoadamantane is converted directly to 1-nitroadamantane by oxidation of the amino group on the carbocyclic ring. The reaction is selective in that only the amine group is affected.

(A) A solution was prepared by mixing together potassium monopersulfate (5.5 g), NaHCO3 (2.5 g), water (200 ml), and acetone, (50 ml). A suspension of 1-aminoadamantane (0.5 g) in acetone (50 ml) was added dropwise and ozone was bubbled into the reaction mixture for about 30 minutes. The reaction was stirred for 2.0 hours at 0 degrees C. Then it was filtered and the filtrate was concentrated on a rotary evaporator. The concentrate was extracted twice with ethyl acetate (2×50 ml) and washed with aqueous HCl and then with brine. H NMR identified a very pure 1-nitroadamantane and the yield was 0.44 g.

(B) A solution was prepared by mixing together potassium monopersulfate (26 g.), NaHCO3 (5.0 g.), water (200 ml), and acetonitrile (70 ml). Ozone was bubbled through the solution while a suspension of 1-aminoadamantane in acetonitrile (2.0 g/100 ml) was added dropwise over 2 hours and at a reaction temperature of 0 degrees. The ozone was stopped and the reaction was stirred overnight. The product was recovered as in (A) above. The yield of 1-nitroadamantane was 0.46 g.

EXAMPLE 2

Preparation of Nitrocubane

Potassium monopersulfate (6.0 g), $NaHCO_3$ (2.0 g), water (20 ml), and acetonitrile, (30 ml) were mixed together. A solution of the hydrochloride salt of 1,3,5,7-tetraaminocubane in water, 100 mg in 25 ml, was slowly added to the solution while ozone was slowly bubbled through the reaction medium. The reaction temperature was room temperature. The addition of ozone was stopped after 4 hours; the yellowish suspension became milky white. The medium was stirred for 4 days. The reaction product was filtered and the filtrate was concentrated on a rotary evaporator. The concentrate was extracted twice with ethyl acetate (2×50 ml) and washed with aqueous HCl and then with brine. H NMR identified a 1,3,5,7-tetranitrocubane product.

EXAMPLE 3

Preparation of Nitrocubane

Potassium monopersulfate (3.0 g), $NaHCO_3$ (1.0 g), water (20 ml), and acetonitrile, (20 ml) were mixed together to form a first solution. A second solution of 1,4-diaminocubane hydrochloride in water, 100 mg in 25 ml, was slowly added to the first solution and the solution was cooled to 0 degrees C. Then, ozone was slowly bubbled through the solution. The reaction mixture turned milky white after one hour. The ozone was stopped and the mixture was stirred overnight. The reaction product was filtered and the filtrate was concentrated on a rotary evaporator. The concentrate was extracted twice with ethyl acetate (2×50 ml) and washed with aqueous HCl and then with brine. H NMR identified a 1,4-dinitrocubane product. Similar results are obtained when acetone is used in place of acetonitrile.

EXAMPLE 4

Preparation of Nitrocubane

Potassium monopersulfate (4.0 g), water (50 ml), and acetonitrile, (15 ml), were mixed together to form a solution. Then, ozone was added until the solution was saturated. A second solution of 1,3,5,7-tetra-aminocubane hydrochloride in water, 200 mg in 15 ml, was slowly added to the first solution while ozone was slowly bubbled through the first solution. The reaction temperature was 0 degrees C. The addition of ozone was stopped after 2 hours; the reaction mixture was stirred overnight and 10 ml of acetone were added.

The reaction product was filtered and the filtrate was concentrated on a rotary evaporator. The concentrate was extracted twice with ethyl acetate (2×50 ml) and washed with aqueous HCl and then with brine. H NMR identified a tetranitrocubane product.

EXAMPLE 5

Preparation of Nitrocubane

A solution of 1,3,5,7-tetraaminocubane hydrochloride was prepared in water, 1000 mg in 200 ml. Ozone was slowly added for 20 minutes and at 0 degrees C. A mixture of potassium monopersulfate and $NaHCO_3$ was added in portions along with 150 ml of acetone. The ozone was discontinued. The reaction suspension became brown and was stirred for 4 hours. The reaction product was filtered and the filtrate was concentrated on a rotary evaporator. The concentrate was extracted with ethyl acetate washed with aqueous HCl and then with brine. H NMR identified a 1,3,5,7-tetranitrocubane product and the yield was 150 mg.

EXAMPLE 6

Preparation of Nitrocubane

A solution was prepared of 1,4-diaminocubane hydrochloride in water, 200 mg in 120 ml. The solution was cooled to 0 degrees C. and ozone was bubbled into it for 20 hours. Then, a mixture of potassium monopersulfate (5.0 g) and NaHCO$_3$ (2.3 g) was added slowly to the solution. 70 ml of acetone was added. After one hour, the ozone was stopped. The mixture was stirred for 5 hours. The reaction product was filtered and the filtrate was concentrated on a rotary evaporator. The concentrate was extracted with ethyl acetate and washed with water, and then with brine. H NMR identified a 1,4-dinitrocubane product and the yield was 60 mg.

EXAMPLE 7

Preparation of Nitro Benzoic Acid

In this example, an amino substituted aromatic compound is converted directly and selectively to the corresponding nitro substituted aromatic compound.

A solution was prepared by mixing potassium monopersulfate (16 g.), NaHCO$_3$ (7.0 g), water (140 ml) and acetonitrile (60 ml). This was saturated with ozone at 0 degrees C. for 30 minutes. Then, a solution of 2-amino-4-nitro benzoic acid (1.0 g) in acetonitrile (30 ml) and water (30 ml) was added dropwise. The mixture was stirred overnight and filtered. The filtrate was washed with acetonitrile and extracted with ethyl acetate (3×20 ml). The solid product was triturated with ether. 0.70 g. of 2,4-dinitrobenzoic were recovered.

In terms of the overall reaction conditions, the process preferably uses organic amines or amine hydrochlorides. The sodium hydrogen carbonate is used in the reaction media so that a pH range of 6 to 7 can be attained. This suppresses the tendency of the amino group to undergo side reactions. In contrast to the aminom substituted compounds, the equivalent polyisocyanate compounds do not convert to the nitro compounds under the reaction conditions described. Both oxidizing agents need to be used to achieve the production of the nitro compounds. The ozone is consumed slowly by the reactants. The preferred monopersulfate is OXONE, TM, monopersulfate compound. It is a potassium peroxy monosulfate.

It can be seen that the process of the invention is a selective, direct oxidation to produce organic nitro compounds. The advantages are clearly demonstrated by the above examples.

I claim:

1. A process of selective, direct oxidation comprising reacting an organic compound having a substrate containing at least one substituent selected from amine and amine hydrochloride groups with a mixture of oxidizing agents consisting essentially of monopersulfates and ozone to convert the amine and amine hydrochloride groups to the corresponding nitro groups while leaving the remainder of the compound intact.

2. The process of claim 1 where the organic compound has one or more oxygen containing functional groups in addition to the amine or amine hydrochloride groups.

3. The process of claim 1 where the organic compound has one or more carboxylic acid functional groups in addition to the amine or amine hydrochloride groups.

4. The process of claim 1 where the reaction is conducted in the presence of a solvent for the organic compound containing the amine or amine hydrochloride groups.

5. The process of claim 1 where the reaction is conducted at a pH in the range of 6 to 7.

6. The process of claim 1 where the monopersulfate is a potassium persulfate and the reaction is conducted at a pH in the range of 6 to 7.

7. The process of claim 1 where the reaction is conducted in the presence of a solvent for the organic compound containing the amine or amine hydrochloride group and the solvent is selected from water, water and acrylonitrile and water and acetone.

8. The process of claim 1 where the reaction is conducted in the presence of a solvent for the organic compound containing the amine or amine hydrochloride group and the solvent is selected from water, water and acrylonitrile and water and acetone and the reaction is conducted at a pH in the range of 6 to 7.

* * * * *